United States Patent
Rebellino

(10) Patent No.: US 10,357,326 B1
(45) Date of Patent: Jul. 23, 2019

(54) MRI BREAST BIOPSY TARGETING GRID AND CUBE

(71) Applicant: Devicor Medical Products, Inc., Cincinnati, OH (US)

(72) Inventor: Justin Rebellino, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 15/664,881

(22) Filed: Jul. 31, 2017

Related U.S. Application Data

(60) Provisional application No. 62/368,647, filed on Jul. 29, 2016.

(51) Int. Cl.
| A61B 10/02 | (2006.01) |
| A61B 5/055 | (2006.01) |
| A61B 90/11 | (2016.01) |

(52) U.S. Cl.
CPC ............ *A61B 90/11* (2016.02); *A61B 5/055* (2013.01); *A61B 10/0233* (2013.01)

(58) Field of Classification Search
CPC ........ A61B 9/11; A61B 5/055; A61B 10/0233
See application file for complete search history.

(56) References Cited

U.S. PATENT DOCUMENTS

| 5,526,822 A | 6/1996 | Burbank et al. |
| 5,855,554 A * | 1/1999 | Schneider ............ A61B 6/0414 378/37 |
| 5,928,164 A | 7/1999 | Burbank et al. |
| 6,017,316 A | 1/2000 | Ritchart et al. |
| 6,086,544 A | 7/2000 | Hibner et al. |
| 6,162,187 A | 12/2000 | Buzzard et al. |
| 6,432,065 B1 | 8/2002 | Burdorff et al. |
| 6,626,849 B2 | 9/2003 | Huitema et al. |
| 6,752,768 B2 | 6/2004 | Burdorff et al. |
| 7,442,171 B2 | 10/2008 | Stephens et al. |
| 7,648,466 B2 | 1/2010 | Stephens et al. |
| 7,831,290 B2 | 11/2010 | Hughes et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,083,687 B2 | 12/2011 | Parihar |

(Continued)

OTHER PUBLICATIONS

U.S. Appl. No. 62/368,647, filed Jul. 29, 2016.

*Primary Examiner* — Sean P Dougherty
(74) *Attorney, Agent, or Firm* — Frost Brown Todd LLC

(57) ABSTRACT

A medical device localization assembly includes an exterior frame, at least one lateral bar, a plurality of locating members and a targeting guide. The exterior frame includes a distal face configured to compress against tissue. The at least one lateral bar extends within the exterior frame and at least one open recess is formed between the lateral bar and the exterior frame. The plurality of locating members are positioned along an inner side of the exterior frame and the at least one lateral bar. The plurality of locating members extend into the at least one open recess and the at least one open recess is configured to removably receive the targeting guide at the proximal face. The plurality of locating members are sized and shaped to removably hold the guide cube such that the plurality of locating members are configured to correspond to the shape of the targeting guide.

19 Claims, 15 Drawing Sheets

(56) References Cited

U.S. PATENT DOCUMENTS

| | | | |
|---|---|---|---|
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,277,394 B2 | 10/2012 | Hibner | |
| 8,328,732 B2 | 12/2012 | Parihar et al. | |
| 8,454,531 B2 | 6/2013 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,486,186 B2 | 11/2016 | Fiebig et al. | |
| 9,999,406 B2 | 6/2018 | Hibner et al. | |
| 2004/0002647 A1* | 1/2004 | Desai | A61B 8/0841 600/417 |
| 2004/0059177 A1* | 3/2004 | Baltas | A61N 5/1007 600/3 |
| 2006/0074345 A1 | 4/2006 | Hibner | |
| 2006/0241385 A1* | 10/2006 | Dietz | A61B 10/0275 600/415 |
| 2007/0233157 A1* | 10/2007 | Mark | A61B 17/3403 606/130 |
| 2007/0255168 A1* | 11/2007 | Hibner | A61B 17/3403 600/562 |
| 2007/0255170 A1* | 11/2007 | Hibner | A61B 10/0266 600/564 |
| 2009/0131821 A1 | 5/2009 | Speeg et al. | |
| 2009/0270725 A1* | 10/2009 | Leimbach | A61B 10/0275 600/431 |
| 2009/0270726 A1* | 10/2009 | Leimbach | A61B 10/0275 600/431 |
| 2009/0270760 A1* | 10/2009 | Leimbach | A61B 10/0275 600/567 |
| 2009/0292224 A1* | 11/2009 | Bowman | A61B 90/11 600/567 |
| 2009/0292244 A1* | 11/2009 | Flagle | A61B 17/3403 604/116 |
| 2010/0152610 A1 | 6/2010 | Parihar et al. | |
| 2010/0160810 A1* | 6/2010 | Parihar | A61B 90/11 600/562 |
| 2010/0160811 A1* | 6/2010 | Parihar | A61B 17/3403 600/562 |
| 2010/0160819 A1 | 6/2010 | Parihar et al. | |
| 2010/0160825 A1* | 6/2010 | Parihar | A61B 17/3403 600/567 |
| 2010/0317990 A1* | 12/2010 | Leimbach | A61B 17/3403 600/562 |
| 2010/0317991 A1* | 12/2010 | Leimbach | A61B 90/17 600/562 |
| 2010/0317992 A1* | 12/2010 | Leimbach | A61B 90/17 600/562 |
| 2010/0317993 A1* | 12/2010 | Leimbach | A61B 10/0275 600/562 |
| 2010/0317994 A1* | 12/2010 | Leimbach | A61B 10/0275 600/562 |
| 2010/0324444 A1* | 12/2010 | Mollere | A61B 10/0233 600/562 |
| 2010/0324445 A1* | 12/2010 | Mollere | A61B 90/17 600/564 |
| 2010/0324448 A1* | 12/2010 | Mollere | A61B 90/17 600/567 |
| 2011/0060393 A1* | 3/2011 | Azure | A61B 18/1477 607/115 |
| 2011/0082364 A1* | 4/2011 | Hibner | A61B 90/17 600/415 |
| 2011/0092847 A1* | 4/2011 | Wale | A61B 10/0275 600/562 |
| 2011/0092848 A1* | 4/2011 | Hibner | A61B 90/17 600/562 |
| 2011/0092849 A1* | 4/2011 | Deshmukh | A61B 90/17 600/562 |
| 2011/0092850 A1* | 4/2011 | Kulkarni | A61B 90/17 600/562 |
| 2011/0092983 A1* | 4/2011 | Pawar | A61B 90/17 606/130 |
| 2011/0257594 A1* | 10/2011 | Lacoursiere | A61B 10/0283 604/117 |
| 2013/0324882 A1 | 12/2013 | Mescher | |
| 2014/0039343 A1 | 2/2014 | Mescher et al. | |
| 2014/0303515 A1* | 10/2014 | Shabaz | A61B 17/3403 600/567 |
| 2015/0025414 A1* | 1/2015 | Rhad | A61B 10/0266 600/567 |
| 2015/0057525 A1* | 2/2015 | Tomiha | A61B 5/0051 600/410 |
| 2015/0065913 A1 | 3/2015 | Keller et al. | |
| 2015/0168509 A1* | 6/2015 | Yang | A61B 10/0233 600/567 |
| 2015/0282880 A1* | 10/2015 | Allaway | A61B 8/0841 600/464 |
| 2016/0228147 A1* | 8/2016 | Darrow | A61B 17/3403 |
| 2016/0354112 A1* | 12/2016 | Kustra | A61B 17/3403 |
| 2017/0014192 A1* | 1/2017 | Bharat | A61B 17/3403 |
| 2017/0203128 A1* | 7/2017 | Kung | A61B 34/20 |

* cited by examiner

MRI BREAST BIOPSY TARGETING GRID AND CUBE

PRIORITY

This application claims priority to U.S. Provisional Application Ser. No. 62/368,647, filed Jul. 29, 2016, entitled "MRI Breast Biopsy Targeting Grid and Cube," the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 21, 2012; U.S. Pat. No. 8,801,742, entitled "Needle Assembly and Blade Assembly for Biopsy Device," issued Aug. 12, 2014; U.S. Pat. No. 8,938,285, entitled "Access Chamber and Markers for Biopsy Device," issued Jan. 20, 2015; and U.S. Pat. No. 8,858,465, entitled "Biopsy Device with Motorized Needle Firing," issued Oct. 14, 2014. The disclosure of each of the above-cited U.S. Patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006, now abandoned; U.S. Pat. Pub. No. 2008/0146962, entitled "Biopsy System with Vacuum Control Module," published Jun. 19, 2008, issued as U.S. Pat. No. 9,095,326 on Aug. 4, 2015; U.S. Pat. Pub. No. 2008/0214955, entitled "Presentation of Biopsy Sample by Biopsy Device," published Sep. 4, 2008, issued as U.S. Pat. No. 9,345,457 on May 24, 2016; U.S. Pat. Pub. No. 2008/0221480, entitled "Biopsy Sample Storage," published Sep. 11, 2008, issued as U.S. Pat. No. 8,118,755 on Feb. 21, 2012; U.S. Pat. Pub. No. 2009/0131821, entitled "Graphical User Interface For Biopsy System Control Module," published May 21, 2009, now abandoned; U.S. Pat. Pub. No. 2009/0131820, entitled "Icon-Based User Interface on Biopsy System Control Module," published May 21, 2009, issued as U.S. Pat. No. 8,454,531 on Jun. 4, 2013; U.S. Pat. Pub. No. 2010/0113973, entitled "Biopsy Device with Rotatable Tissue Sample Holder," published May 6, 2010, issued as U.S. Pat. No. 8,241,226 on Aug. 14, 2012; U.S. Pat. Pub. No. 2010/0152610, entitled "Hand Actuated Tetherless Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2010/0160824, entitled "Biopsy Device with Discrete Tissue Chambers," published Jun. 24, 2010, issued as U.S. Pat. No. 8,702,623 on Apr. 22, 2014; U.S. Pat. Pub. No. 2010/0317997, entitled "Tetherless Biopsy Device with Reusable Portion," published Dec. 16, 2010, issued as U.S. Pat. No. 8,206,316 on Jun. 26, 2012; U.S. Pat. Pub. No. 2012/0109007, entitled "Handheld Biopsy Device with Needle Firing," published May 3, 2012, issued as U.S. Pat. No. 8,764,680 on Jul. 1, 2014; U.S. Pat. Pub. No. 2013/0053724, entitled "Biopsy Device Tissue Sample Holder with Bulk Chamber and Pathology Chamber," published Feb. 28, 2013, issued as U.S. Pat. No. 9,326,755 on May 3, 2016; U.S. Pat. Pub. No. 2013/0144188, entitled "Biopsy Device With Slide-In Probe," published Jun. 6, 2013, issued as U.S. Pat. No. 9,486,186 on Nov. 8, 2016; and U.S. Pat. Pub. No. 2013/0324882, entitled "Control for Biopsy Device," published Dec. 5, 2013, now abandoned. The disclosure of each of the above-cited U.S. Patent Application Publications, U.S. Non-Provisional Patent Applications, and U.S. Provisional Patent Applications is incorporated by reference herein.

In U.S. Pat. Pub. No. 2005/0283069, entitled "MRI Biopsy Device Localization Fixture" published Dec. 22, 2005, issued as U.S. Pat. No. 7,831,290 on Nov. 9, 2010, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
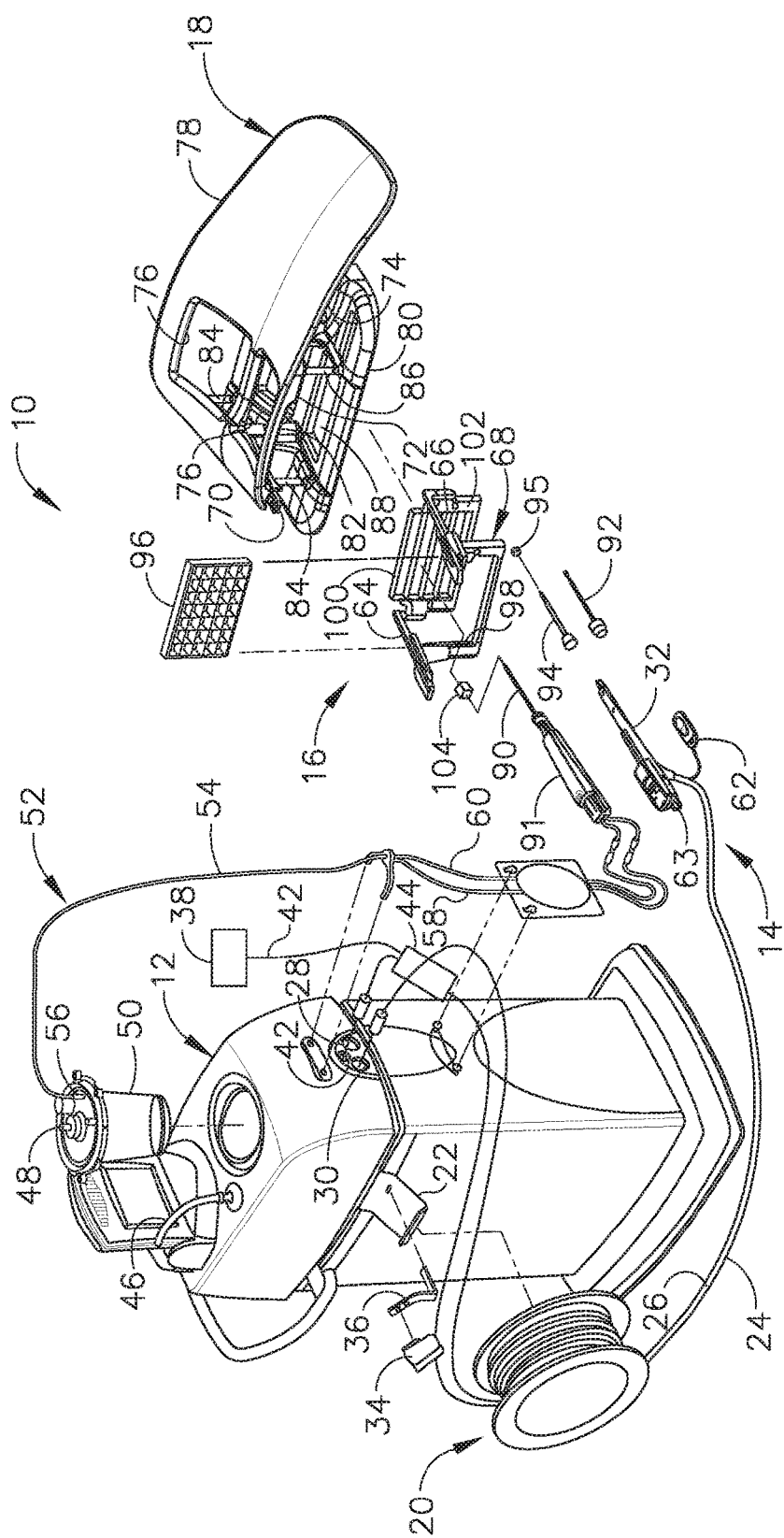
FIG. 1 depicts a perspective view of a biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. OVERVIEW OF EXEMPLARY MRI BIOPSY CONTROL MODULE

Figure 2:
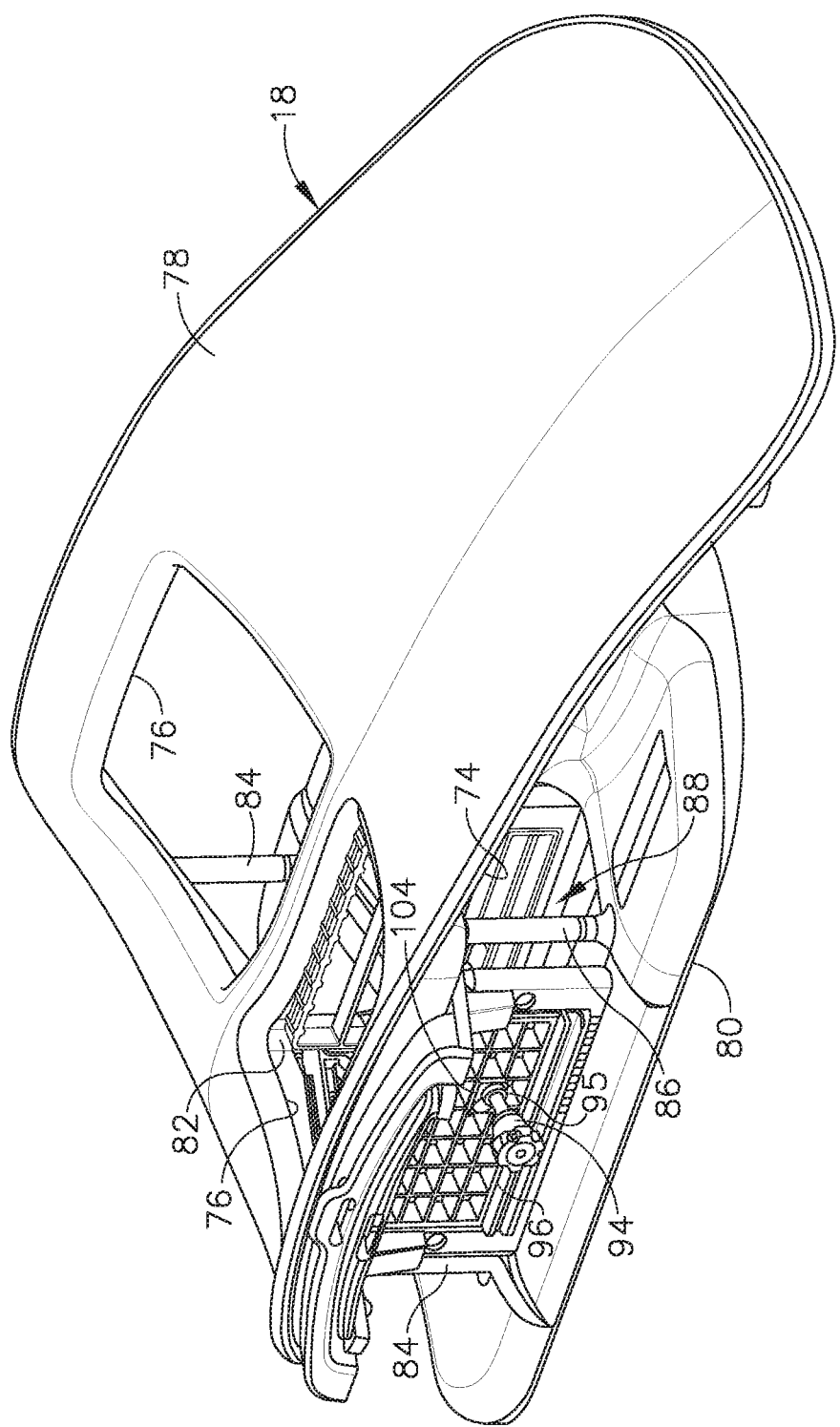
FIG. 2 depicts a perspective view of a breast coil receiving the localization fixture of FIG. 1.
Figure 3:
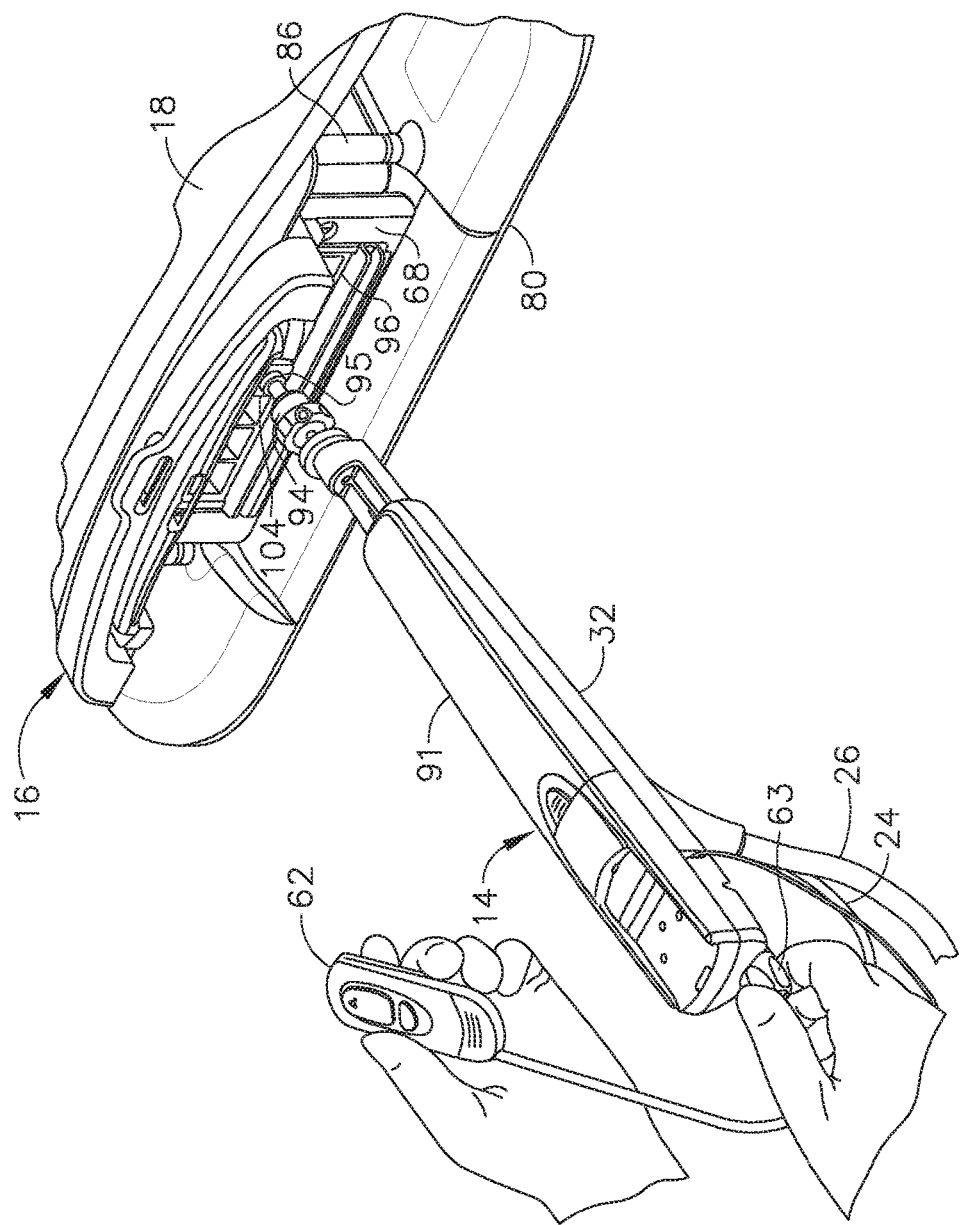
FIG. 3 depicts a perspective view of the biopsy device inserted through the rotatable cube within the cube plate of the localization fixture attached to the breast coil of FIG. 2.

In FIGS. 1-3, an MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. Pat. No. 8,328,732, entitled "Control Module Interface for MRI Biopsy Device," issued Dec. 11, 2012, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. EXEMPLARY LOCALIZATION ASSEMBLY

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. EXEMPLARY BIOPSY DEVICE

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 7:
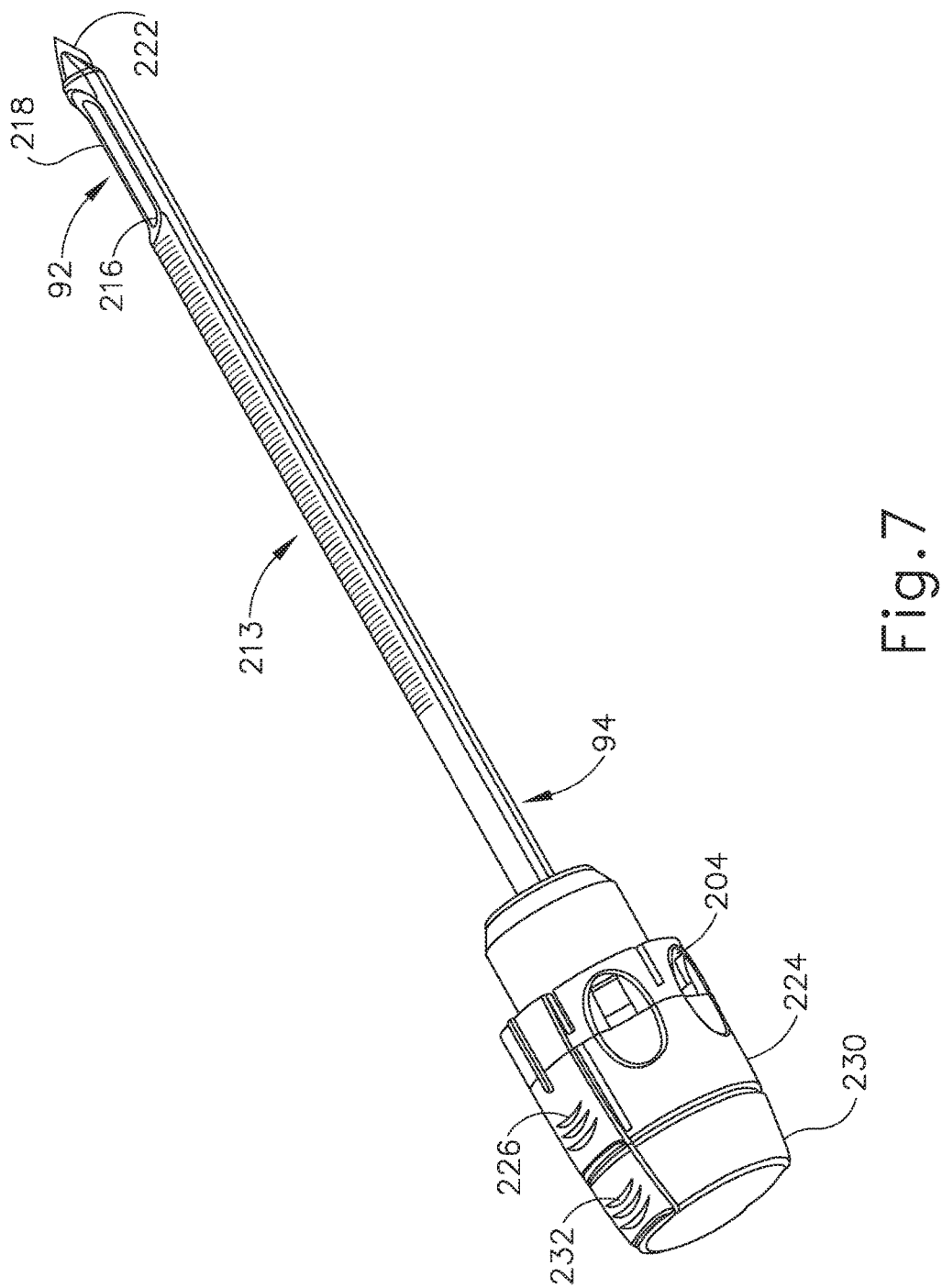
FIG. 7 depicts a perspective view of an obturator and cannula of the biopsy system of FIG. 1.
Figure 8:
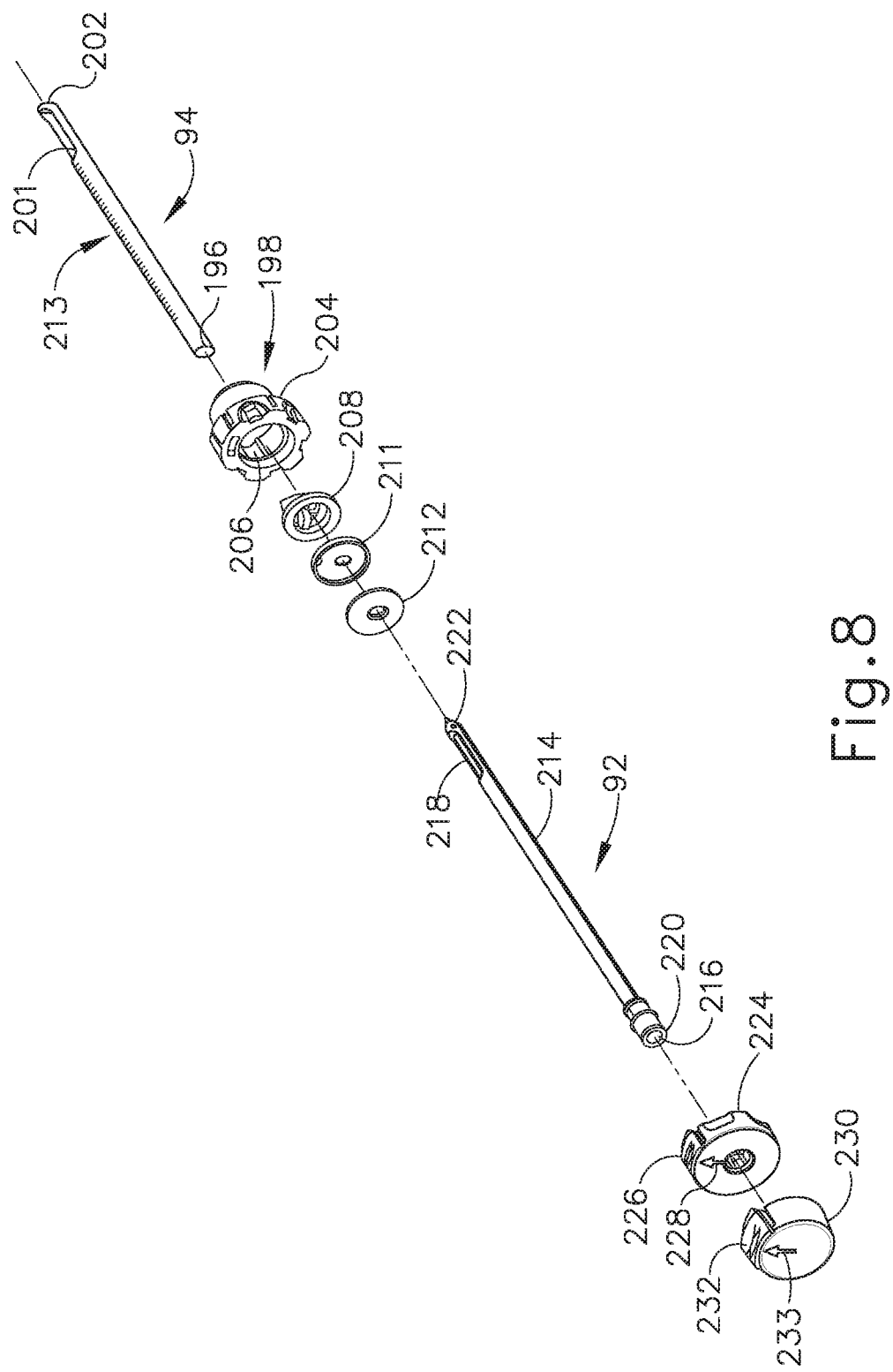
FIG. 8 depicts a perspective exploded view of the obturator and cannula of FIG. 7.
Figure 9:
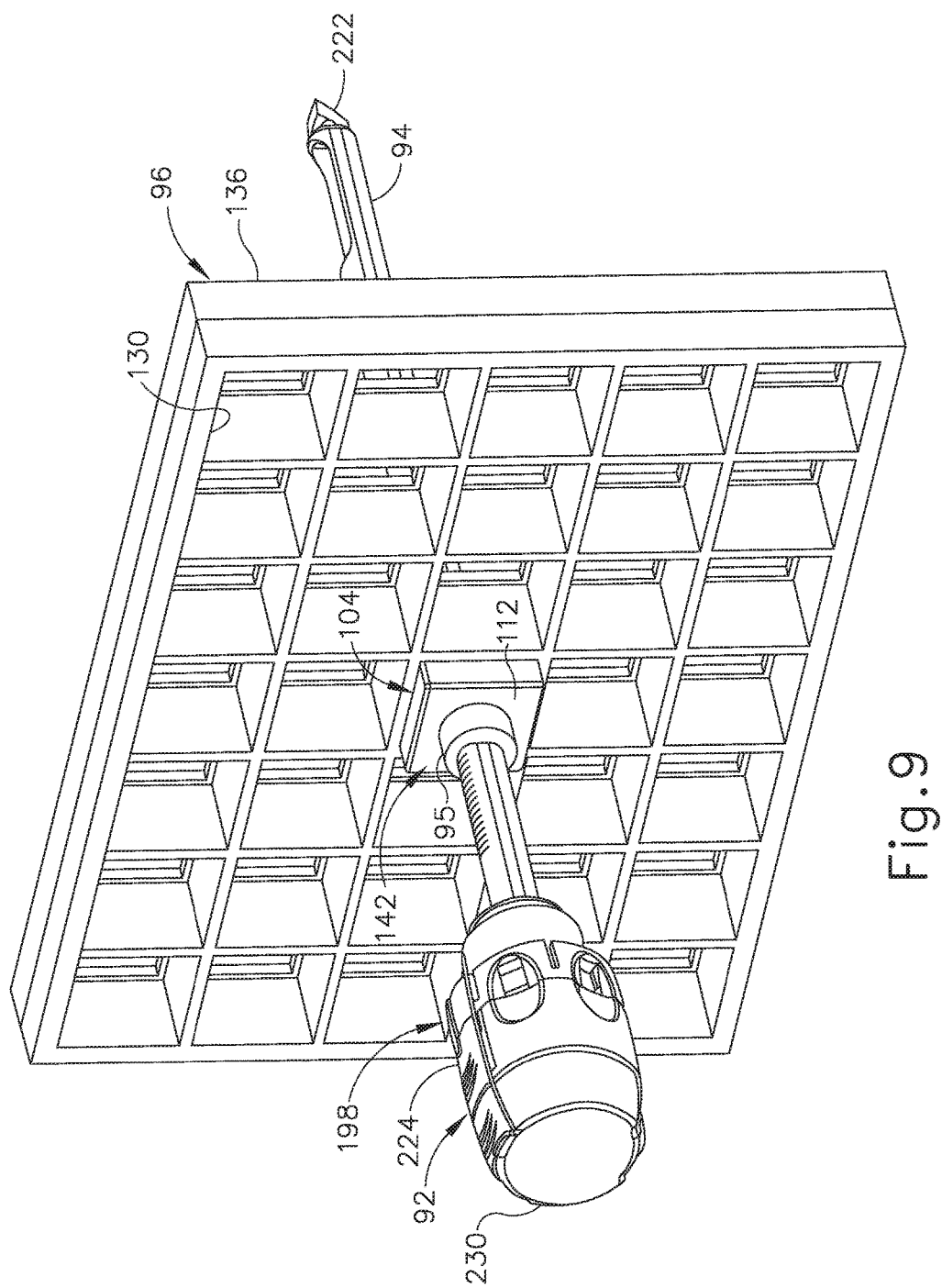
FIG. 9 depicts a perspective view of the obturator and cannula of FIG. 7 with a depth stop device of FIG. 1 inserted through the guide cube and grid plate of FIG. 6.

In the present example, a targeting set (89) comprising cannula (94) and obturator (92) is associated with probe (91). In particular, and as shown in FIGS. 7, 8, and 9, obturator (92) is slid into cannula (94) and the combination is guided through guide cube (104) to the biopsy site within the breast tissue. As shown in FIG. 3, obturator (92) is then withdrawn from cannula (94), then needle (90) of probe (91) is inserted in cannula (94), and then biopsy device (14) is operated to acquire one or more tissue samples from the breast via needle (90).

As best seen in FIG. 8, cannula (94) of the present example is proximally attached to cylindrical hub (198) and cannula (94) includes lumen (196) and lateral aperture (201) proximate to open distal end (202). Cylindrical hub (198) has exteriorly presented thumbwheel (204) for rotating lateral aperture (201). Cylindrical hub (198) has interior recess (206) that encompasses duckbill seal (208), wiper seal (211) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. For instance, obturator (92) includes a shaft (214) that includes fluid lumen (216) that communicates between imageable side notch (218) and proximal port (220). Shaft (214) is longitudinally sized such that piercing tip (222) extends out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (201) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 9, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop device (95). Depth stop device (95) may be of any suitable configuration that is operable to prevent cannula (94) and obturator (92) (or needle (90)) from being inserted further than desired. For instance, depth stop device (95) may be positioned on the exterior of cannula (94) (or needle (90)), and may be configured to restrict the extent to which cannula (94) is inserted into a guide cube. It should be understood that such restriction by depth stop device (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stop devices (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (201) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (201) of cannula (94) and the lateral aperture of needle (90). Severed tissue samples may be retrieved from biopsy device (14) in any suitable fashion.

It should be understood that although biopsy system (10) is discussed above as utilizing disposable probe assembly (91), other suitable probe assemblies and biopsy device assemblies may be utilized. By way of example only, other suitable biopsy devices may be configured and operable in accordance with at least some of the teachings of U.S. Pat. No. 8,206,316, entitled "Tetherless Biopsy Device with Reusable Portion," issued Jun. 26, 2012, the disclosure of which is incorporated by reference herein; U.S. Pat. No. 8,277,394, entitled "Multi-Button Biopsy Device," issued Oct. 2, 2012, the disclosure of which is incorporated by reference herein; and/or U.S. Pub. No. 2012/0065542, entitled "Biopsy Device Tissue Sample Holder with Removable Tray," published Mar. 15, 2012, the disclosure of which is incorporated by reference herein. As yet another merely illustrative example, other suitable biopsy devices may be configured and operable in accordance with at least some of the teachings of U.S. Pub. No. 2010/0160824, the disclosure of which is incorporated by reference herein; U.S. Patent Pub. No. 2013/0144188, entitled "Biopsy Device with Slide-In Probe," published Jun. 6, 2013, the disclosure of which is incorporated by reference herein; U.S. Patent Pub. No. 2013/0324882, entitled "Control for Biopsy Device," published Dec. 5, 2013, the disclosure of which is incorporated by reference herein; U.S. Patent Pub. No. 2014/0039343, entitled "Biopsy System," published Feb. 6, 2014, the disclosure of which is incorporated by reference herein; and/or U.S. Patent Pub. No. 2015/0065913, entitled "Tissue Collection Assembly for Biopsy Device," published Mar. 5, 2015, the disclosure of which is incorporated by reference herein.

Still other suitable forms of biopsy devices that may be used in conjunction with the various alternative components of system (10) as described herein will be apparent to those of ordinary skill in the art.

IV. EXEMPLARY GUIDE CUBE

In some versions, a guide cube may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 4:
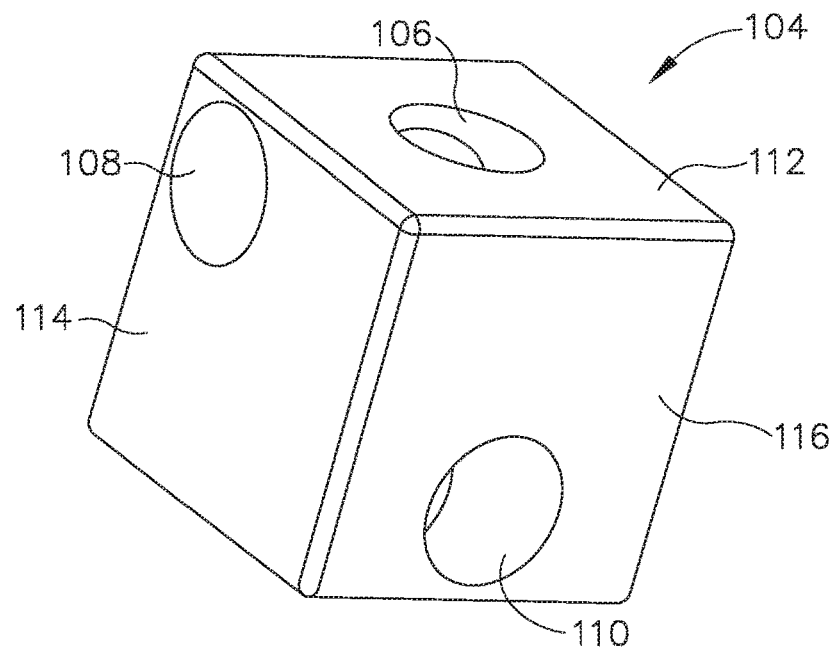
FIG. 4 depicts a perspective view of a two-axis rotatable guide cube of the biopsy system of FIG. 1.
Figure 5:
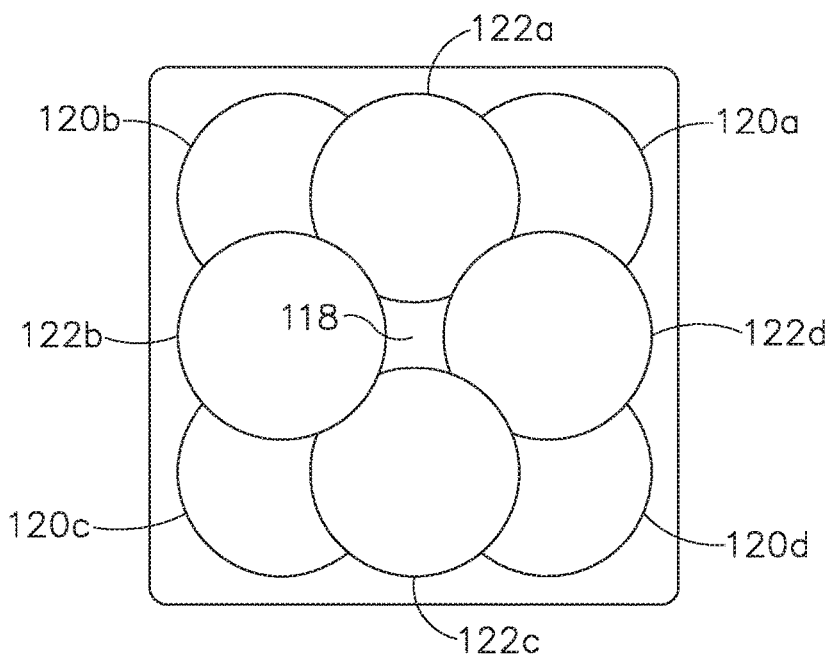
FIG. 5 depicts a diagram of nine guide positions achievable by the two-axis rotatable guide cube of FIG. 4.

In FIG. 4, guide cube (104) includes a central guide hole (106), a corner guide hole (108), and an off-center guide hole (110) that pass orthogonally to one another between respective opposite pairs of faces (112, 114, 116). By selectively rotating guide cube (104) in two axis, one of pairs of faces (112, 114, 116) may be proximally aligned to an unturned position and then selected proximal face (112, 114, 116) optionally rotated a quarter turn, half turn, or three quarter turn. Thereby, one of nine guide positions (118) (i.e., using central guide hole (106)), (120a-120d) (i.e., corner guide hole (108)), (122a-122d) (i.e., using off-center guide hole (110)) may be proximally exposed as depicted in FIG. 5.

Figure 6:
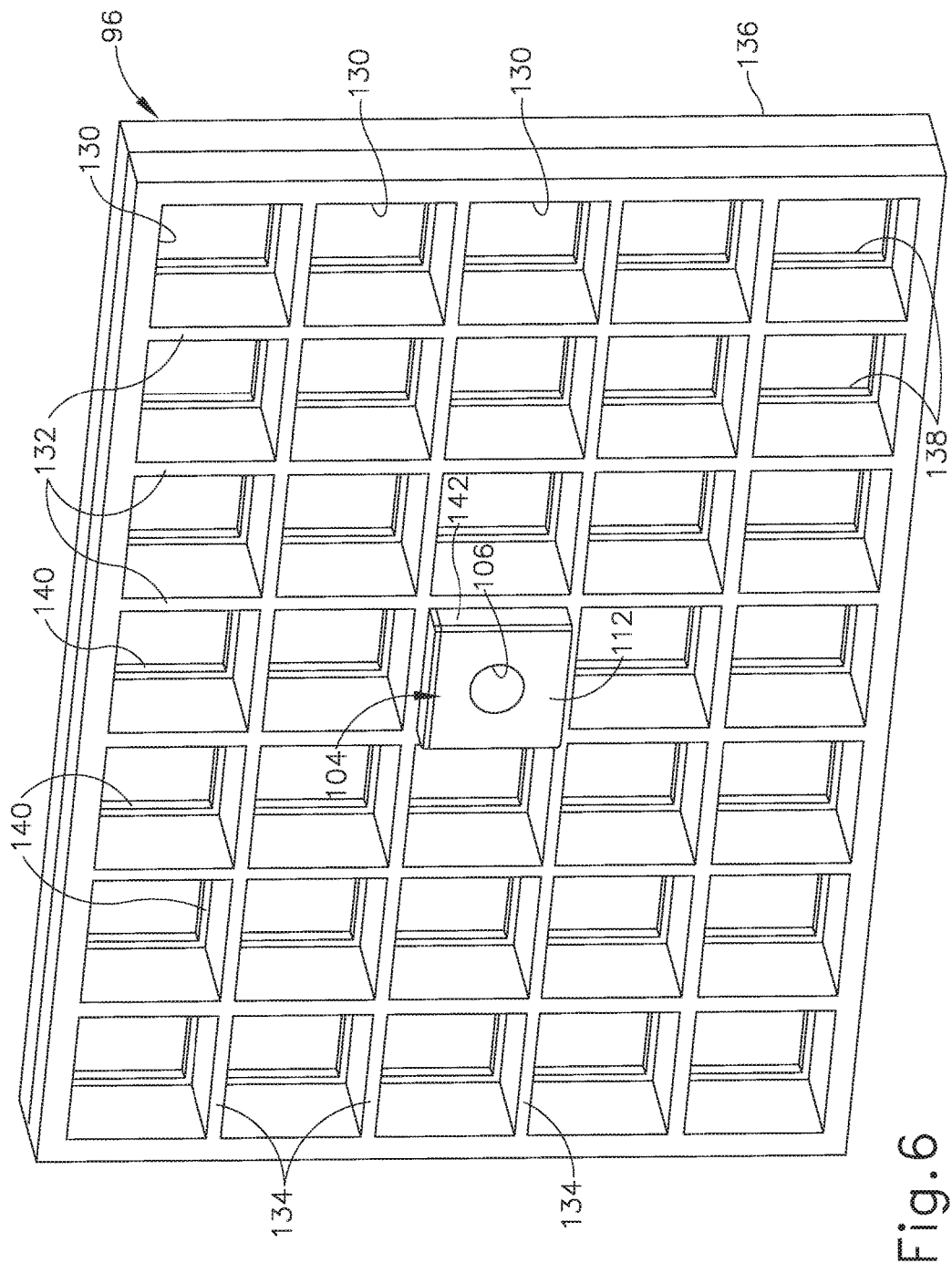
FIG. 6 depicts a perspective view of a two-axis rotatable guide cube into a lateral grid with the backing of the localization fixture of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

In some other versions, guide cube (104) is replaced with an alternative guide cube or other guide structure that is configured and operable in accordance with at least some of the teachings of U.S. Pat. Pub. No. 2015/0025414, entitled "Biopsy Device Targeting Features," published Jan. 22, 2015, the disclosure of which is incorporated by reference herein.

V. EXEMPLARY OPEN RECESSED GRID PLATE WITH ADJUSTABLE TARGETING MEANS

In some instances, it may be desirable for an MRI targeting grid plate to comprise a body defined by fewer edges or walls to provide less restrictive passages for selectively positioning a guide cube therein. A guide plate comprising a plurality of vertical bars (132) and horizontal bars (134) thereby creates distinct square recesses (130) for inserting a guide cube therein. However, a lesion located in a patient's breast, or another area of interest, may not be precisely aligned with one of the plurality of square recesses (130). For example, an identified lesion may be covered by one of the plurality of vertical bars (132) or horizontal bars (134). In this instance, an operator may experience difficulty extracting the lesion, or may be required to remove the guide plate entirely to reposition the guide plate before proceeding with the biopsy procedure, due to the limited access created by the plurality of impediments created by bars (132, 134). This obstacle may prove to be time consuming and costly. Providing a grid plate that does not include a plurality of distinct square recesses defined by the intersection of numerous vertical bars (132) and horizontals bars (134) may be beneficial to allow a guide cube to be selectively positioned within the guide plate in a better orientation with the lesion or area of interest.

In grid plates such as grid plate (96) described above, it may be beneficial to reduce or remove the number of vertical bars (132) and/or horizontal bars (136) comprised therein, such that an operator is provided greater access to position the guide cube adjacent to the target lesion and other nearby areas of interest. Furthermore, it may be desirable for a guide cube to be configured to be adjustable relative to the grid plate to thereby further improve the ability to selectively position the guide cube along the grid plate in relation to the location of an area of interest within the patient's breast. For example, a guide cube that is structurally configured to associate with the less restrictive passage configuration of the exemplary alternative grid plate described above may be beneficial to easily maneuver the guide cube to a desirable biopsy location relative to the patient's body.

The following description provides various examples of a grid plate and corresponding guide cube that are cooperatively configured to effectively position the guide cube in an ideal orientation in relation to the location of a lesion in a patient's breast. Ultimately, providing an uncluttered configuration for a grid plate may be beneficial to increase visibility for an operator, create a simpler user experience when targeting lesions, and improve the probability that an area of interest within a patient's body may be successfully extracted by a biopsy device. It should be understood that the grid plate and guide cube features described below may be readily incorporated into any of the various grid plates (92), guide cubes (104), and biopsy devices (14) described above; and in any of the various surgical procedures described in the various references described herein. Other suitable ways in which the below-described grid plates and guide cubes may be used will be apparent to those of ordinary skill in the art in view of the teachings herein.

A. Open Recessed Grid Plate with Locating Features

Figure 10:
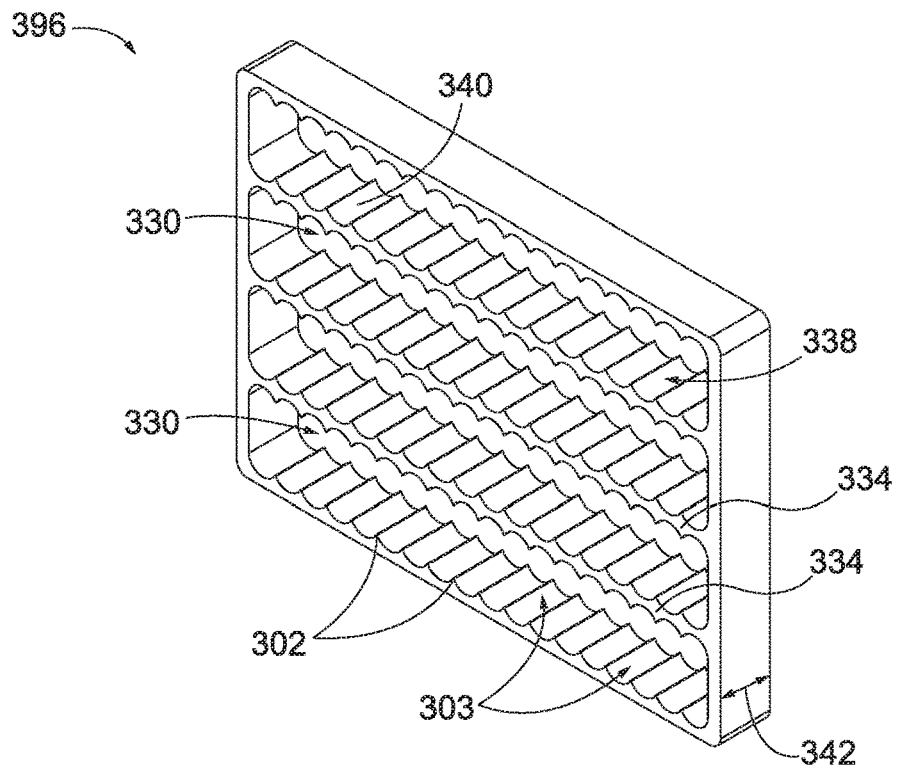
FIG. 10 depicts a perspective view of an exemplary alternative grid plate including a series of horizontal bars and a plurality of locating features.

FIG. 10 shows an exemplary alternative grid plate (396) for use in association with laterally adjustable outer three-sided plate bracket (98) as similarly described above. Except as otherwise provided below, grid plate (396) is configured and operable like grid plate (96) described above. Grid plate (396) comprises horizontal bars (334) extending laterally from one side of grid plate (396) to another, thereby forming open recesses (330). Unlike grid plate (96), grid plate (396) does not include a plurality of structures similar to vertical bars (132) extending vertically from the top to the bottom of grid plate (396). However, as will be described in greater detail below, grid plate (396) may include one or more vertical bars while preserving the increased access and visibility created by the overall reduction of bars extending through open recesses (330).

Grid plate (396) further includes a plurality of locating features or members (302) arranged laterally along horizontal bars (334) and extending into open recesses (330). Locating features (302) are configured to correspond to a shape and size of guide cube or fixture (604) such that locating features are operable to receive and securely hold guide cubes or fixtures (604) therein. In other words, locating features (302) are configured to compress against guide cube or fixture (604) when slidably receiving guide cube or fixture (604) therein. In some versions, similar to grid plate (96), grid plate (396) may include certain features along horizontal bar (334) to securely maintain guide cube or fixture (604) within open recesses (330). By way of example only, open recesses (330) may include a narrowing opening as open recesses (330) extends from a proximal face to a distal face of grid plate (396). This narrowing configuration may provide an enhanced compression fit between grid plate (396) and guide cube or fixture (604). In other versions, grid plate (396) may include a lip that is configured to create a mechanical ground within open recesses (330) to thereby prevent guide cube or fixture (604) from being distally pushed out of the distal face of grid plate (396).

Figure 11:
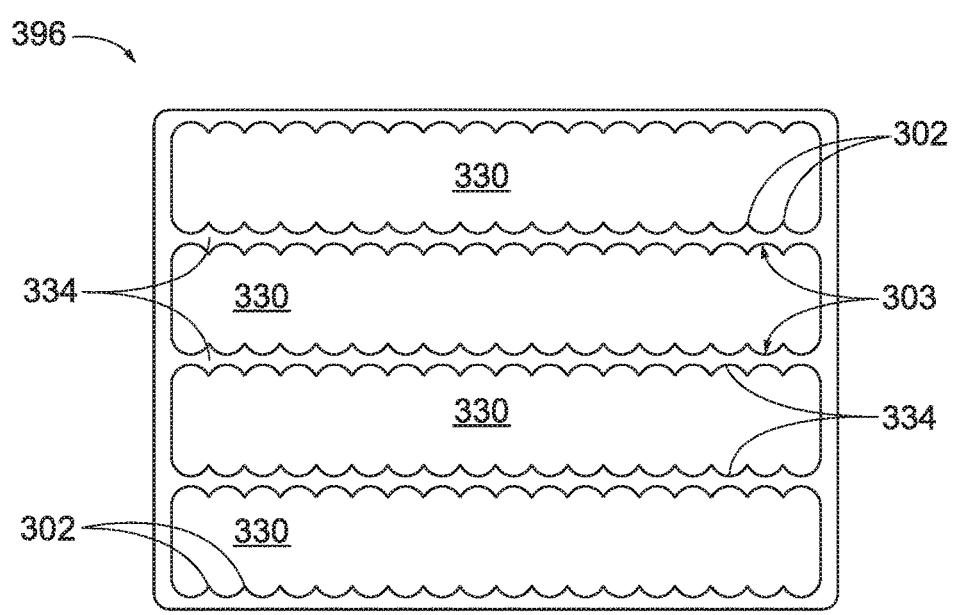
FIG. 11 depicts a front elevational view of the grid plate of FIG. 10.

As best seen in FIG. 11, locating features (302) are formed to have a concave profile (303), configured to correspond to a convex shape (603) of guide cube or fixture (604) such that open recesses (330) are operable to fittingly receive guide cubes or fixtures (604) between locating features (302). As will be described in greater detail below, the concave profile (303) of locating features (302) provide a mating fit with the convex shape (603) of guide holes (606, 608, 610), which increases the surface area of guide cube or fixture (604) that is contacted by grid plate (396).

In the present example, locating features (302) are arranged along horizontal bar (334) in a consecutive pattern such that each locating feature (302) is immediately adjacent to another locating feature (302) along the length of horizontal bar (334). Locating features (302) extend from horizontal bar (334) into open recesses (330) in this repetitious pattern thereby forming concave profiles (303) therebetween each locating feature (302). For example, locating features (302) are arranged in a side-by-side pattern to collectively form a wave-like or sawtooth-like profile.

Furthermore, locating features (302) are positioned along both an upper and lower side of horizontal bar (334) such that each locating feature (302) extends into open recesses (330) and towards an oppositely extending locating feature (302) extending from another horizontal bar (334). In this instance, each symmetrically opposing locating feature (302) forms a distinct locking position relative to the lateral length of horizontal bar (334) to receive guide cube or fixture (604) therein. Although not shown, it should be understood that locating features (302) may be arranged along horizontal bar (334) in various other patterns, spacing, or configurations as shown in the present example. As merely an illustrative example, horizontal bar (334) may include a spacing between each locating feature (302), locating feature (302) may only extend from one side of horizontal bar (334), or as will be described in greater detail below, horizontal bar (334) may cease to include any locating features (334) (see FIG. 19). Other various suitable patterns or arrangements of locating features (302) along horizontal bar (334) will be apparent to those of ordinary skill in the art in view of the teachings herein.

Figure 19:
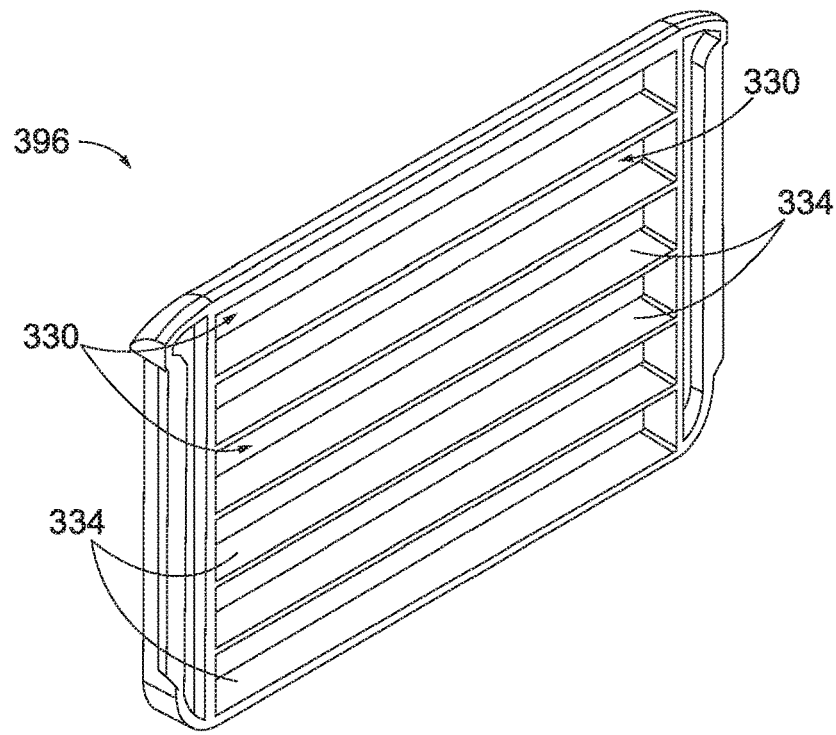
FIG. 19 depicts a perspective view of another exemplary variation of the grid plate of FIG. 10, including a series of horizontal bars without locating features.

Locating features (302) are integral with grid plate (396) such that locating features (302) are formed of a hard, rigid plastic material. Although not shown, it should be understood that locating features (302) may be separate components attached to grid plate (396). In other versions, open recesses (330) may not include any locating features (302) such that guide cube or fixture (604) may be positioned within open recesses (330) freely without obstacle, as shown in FIG. 19. Open recesses (330) are configured to provide greater space for grid plate (396) to receive certain targeting cubes that accommodate larger needle sizes that are not able to be received within other grid plates having smaller recesses. Examples of probe tips or needles that may be used in conjunction with grid plate (396) due to the greater access provided through open recesses (330) are the Mammotome® Legacy 8-Guage and Mammotome® Legacy 11-Guage Probe Tips.

Figure 17:
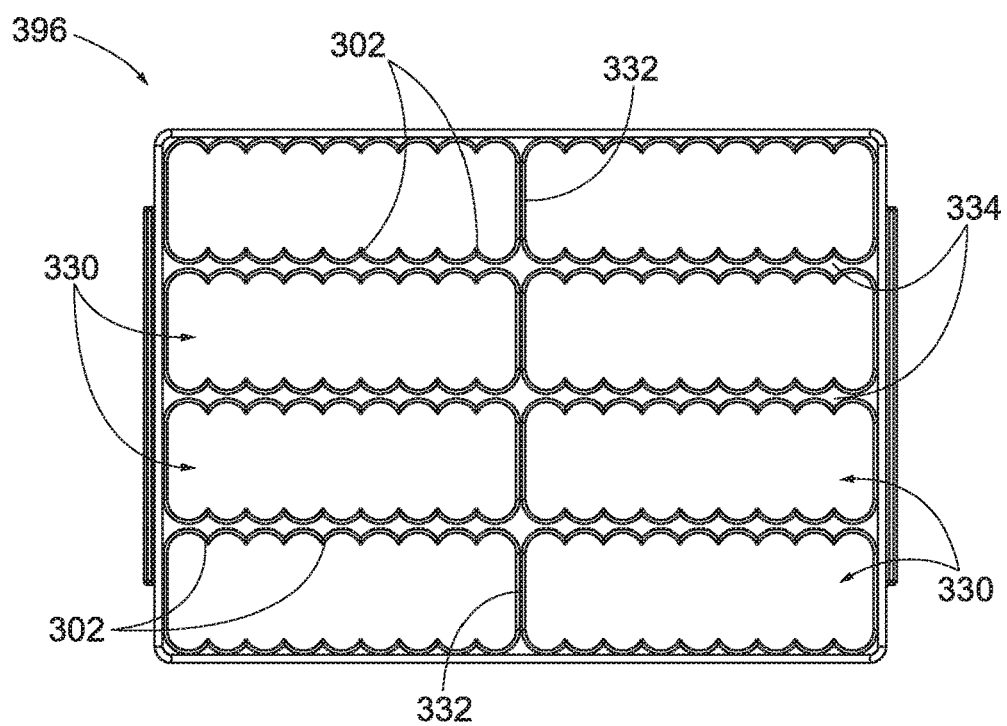
FIG. 17 depicts a front elevational view of an exemplary variation of the grid plate of FIG. 10, including a vertical bar.
Figure 18:
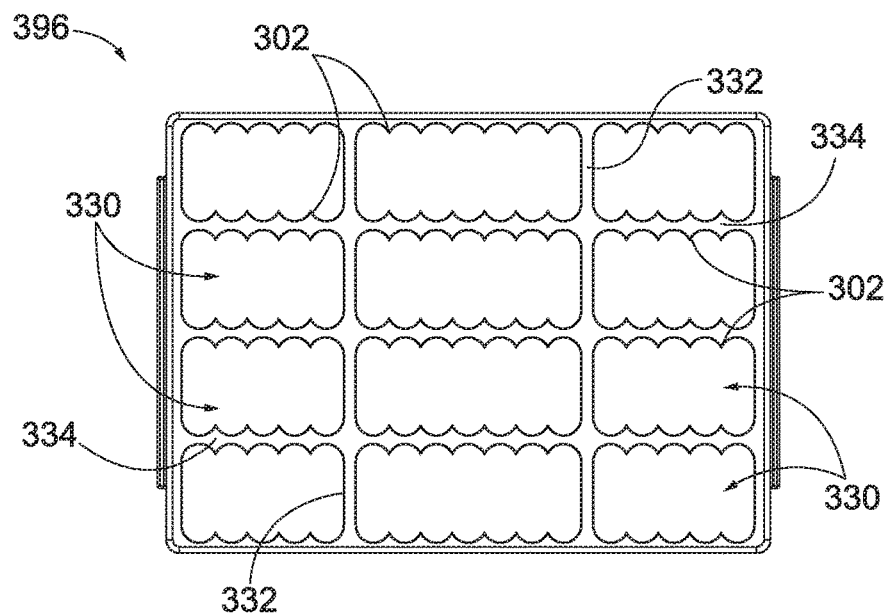
FIG. 18 depicts a front elevational view of another exemplary variation of the grid plate of FIG. 10, including multiple vertical bars.

In other versions, as briefly discussed above and as seen in FIG. 17, grid plate (396) includes a vertical bar (332) extending vertically through a middle portion of grid plate (396). In this instance, open recesses (330) are divided into more defined passages for receiving guide cube or fixture (604). However, in contrast to grid plate (96), grid plate (396) continues to provide greater access and visibility to an operator to perform a biopsy procedure in relation to a target lesion in a breast tissue. As seen in FIG. 18, grid plate (396) includes more than one vertical bar (332) extending perpendicularly through horizontal bars (334). Vertical bars (332) are positioned in relation to horizontal bars (334) such that grid plate (396) remains operable to receive and hold guide cubes or fixtures (604, 704), unlike grid plate (96) which includes a plurality of vertical bars (132). In each version described above, grid plate (396) includes fewer horizontal bars (334) and vertical bars (332) than grid plate (96).

B. Single Orientation Guide Cube

Figure 12:
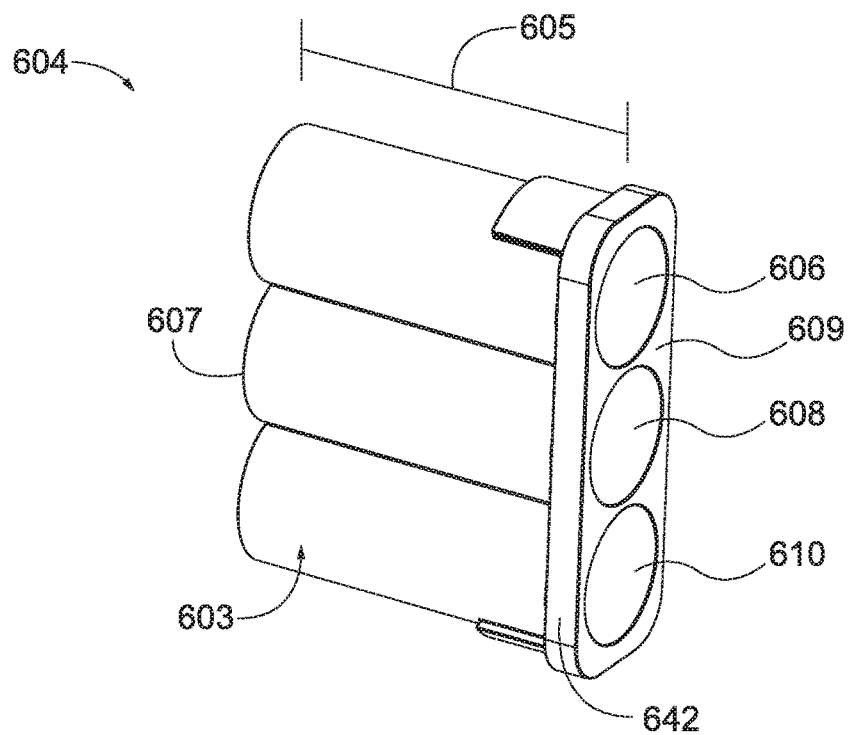
FIG. 12 depicts a perspective view of an exemplary alternative guide cube, including a single orientation of three guide holes.
Figure 13:
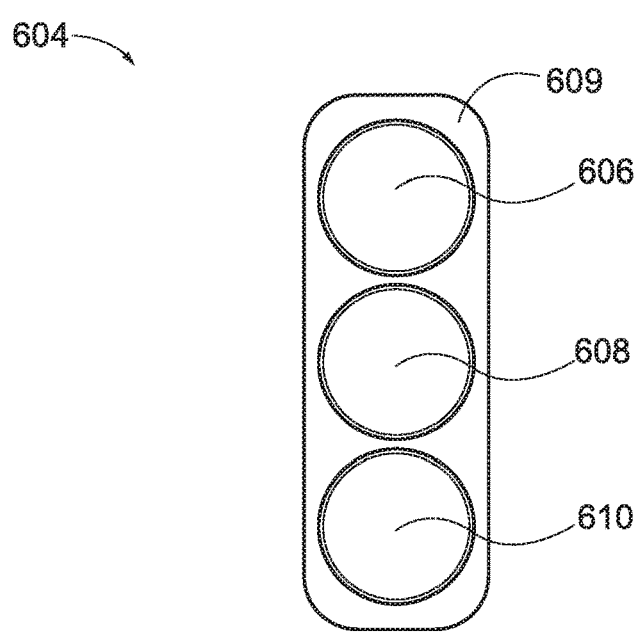
FIG. 13 depicts a front elevational view of the guide cube of FIG. 12.

As seen in FIGS. 12-13, guide cube or fixture (604) comprises guide holes (306, 308, 310) having a circular profile and positioned atop one another in a longitudinal arrangement. As will be discussed in greater detail below, although guide cube or fixture (604) is shown in a three-hole orientation, it should be understood that guide cube or fixture (604) may include more or less guide holes (606, 608, 610). It should be further understood that use of the term "guide cube" herein is not intended to imply that guide cube or fixture (604) must include a cubical shape. Rather, guide cube or fixture (604) may comprise various shapes or profiles, including but not limited to, rectangular, triangular, circular, and/or other suitable shapes as will be apparent to those of ordinary skill in the art in view of the teachings herein. As such, guide cube or fixture (604) may similarly be referred to as a guide fixture, targeting guide, or targeter. Guide cube or fixture (604) is sized and shaped for insertion into a proximal side of open recesses (330) of grid plate (396), opposite a distal side adjacent to the breast tissue. In the present example, as discussed above, guide cube or fixture (604) has a convex shape (603) configured to correspond to the concave profile (303) of locating features (302), such that guide cube or fixture (604) is configured to fit within locating features (302) and thereby be securely held by open recesses (330). Concave profile (303) of locating features (302) is configured to associate with convex shape (603) of the top and bottom guide holes (606, 610) of guide cube or fixture (604).

With guide holes (606, 608, 610) slidably received between a top and bottom locating feature (302), guide fixture (604) is securely held within open recesses (330) with respect to the lateral movability of guide cube or fixture (604). In other words, guide cube or fixture (604) is prevented from laterally translating within open recesses (330) once guide holes (606, 608, 610) are received and engaged by locating features (302). However, guide cube or fixture (604) remains unrestricted with respect to the vertical movability of guide cube or fixture (604) in relation to grid plate (396). In other words, with guide holes (606, 608, 610) slidably received between locating features (302), guide cube or fixture (604) is able to axially translate outwardly from open recesses (330) along the z-axis. Although not shown, it should be understood that locating features (302) of open recesses (330) and guide cube or fixture (604) can have various corresponding shapes or profiles as will be apparent to those of ordinary skill in the art. As merely an illustrative example, locating features (302) may be formed with a convex profile with guide holes (606, 608, 610) of guide cube or fixture (604) having a corresponding concave shape.

As best seen in FIG. 12, guide cube or fixture (604) includes a depth (605) that is greater than a thickness (342) of open recesses (330) of grid plate (396), thereby exposing a proximal portion (642) of guide cube or fixture (604) for seizing and extracting guide cube or fixture (604) from grid plate (396). Guide cube or fixture (604) is prevented from passing through grid plate (396) by the compressive fit between open recesses (330) and guide holes (606, 608, 610) of guide cube or fixture (604). In other words, open recesses (330) are sized and shaped to correspond to the size and shape of guide cube or fixture (604) such that guide cube or fixture (604) is removably retained between locating features (302). With locating features (302) engaging convex shape (603) of guide holes (606, 608, 610), guide cube or fixture (604) is laterally secured within grid plate (396). In addition, open recesses (330) vertically secure guide cube or fixture (604) in grid plate (396) through the frictional engagement between open recesses (330) and guide holes (606, 608, 610).

In the present example, guide cube or fixture (604) is slidably inserted into a preferred open recess (330) of grid plate (396) by aligning top and bottom grid holes (606, 610) with a pair of locating features (302). Once inserted, an operator exerts an axial force onto a distal end (609) of guide cube or fixture (604) to thereby securely engage guide cube or fixture (604) to grid plate (396) with respect to the z-axis. In this instance, proximal portion (642) and distal end (609) of guide cube or fixture (604) extends above a proximal face of grid plate (396), with the proximal face being opposite to the patient's tissue, such that an operator grasps proximal portion (642) to removably disengage guide cube or fixture (604) from the frictional fit with open recesses (330). In some versions, guide cube or fixture (604) and grid plate (396) may be cooperatively configured to include a snap-fit mechanism, such that guide cube or fixture (604) snaps into a secured position within grid plate (396). Although not shown, other various suitable ways in which guide cube (or fixture 604) may removably engage grid plate (396) will be apparent to those of ordinary skill in the art in view of the teachings herein.

Figure 15:
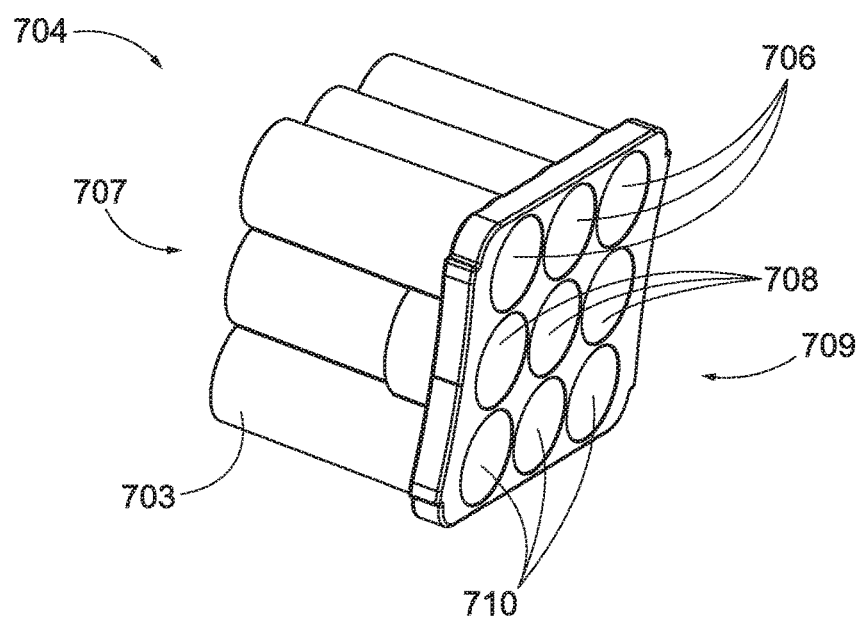
FIG. 15 depicts a perspective view of an exemplary alternative guide cube, including a single orientation of nine guide holes.
Figure 16:
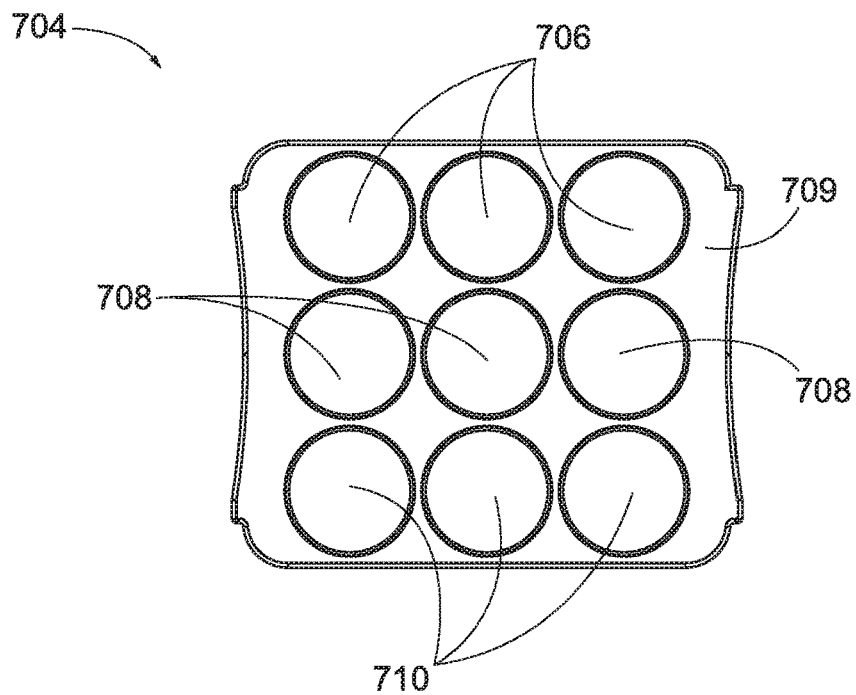
FIG. 16 depicts a front elevational view of the guide cube of FIG. 15.

FIGS. 15-16 shows an exemplary variation guide cube or fixture (704) comprising guide holes (706, 708, 710) having a circular profile and positioned atop and adjacent to one another in consecutive columns. Guide holes (706, 708, 710) are in the form of a nine-hole targeting design, arranged in a three by three (rows and columns, respectively) formation such that guide cube or fixture (704) forms a squared outline with nine circular holes (706, 708, 710) contained therein. Except as otherwise provided below, guide cube or fixture (704) is configured and operable like guide cube (104, 604) described above. Guide cube or fixture (704) is sized and shaped for insertion into a proximal side of open recesses (330) of grid plate (396), opposite a distal side adjacent to the breast tissue. In the present example, similar to guide cube or fixture (604), guide holes (706, 708, 710) have a convex shape (703) configured to correspond to concave profile (303) of locating features (302), such that guide holes (706, 708, 710) are configured to fittingly slide within concave profiles (303) of locating features (302). In this instance, concave profiles (303) of locating features (302) provide a matching fit with convex shape (703) of guide holes (706, 708, 710), which increase the surface area of guide cube or fixture (704) that is contacted by grid plate (396). With guide holes (706, 708, 710) positioned between locating features (302), guide cube or fixture (704) is laterally secured in open recesses (330) with respect to grid plate (396).

Figure 14:
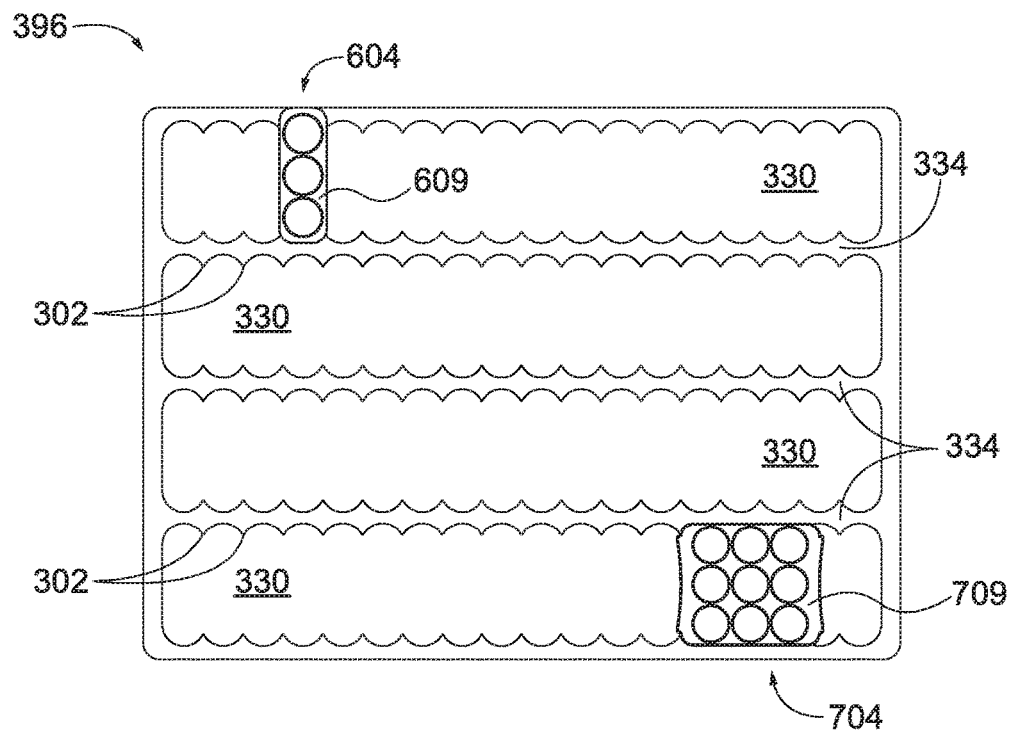
FIG. 14 depicts a front elevational view of the guide cube of FIG. 11 and FIG. 15 selectively positioned within the grid plate of FIG. 10.

As discussed above, it should be understood that locating features (302) of open recesses (330) and guide cube or fixture (704) can have various corresponding shapes or profiles as will be apparent to those of ordinary skill in the art. As merely an illustrative example, locating features (302) may be formed with a convex profile with guide holes (706, 708, 710) of guide cube or fixture (704) having a corresponding concave shape. Due to the larger arrangement of guide holes (706, 708, 710) of guide cube or fixture (704) compared to guide holes (606, 608, 610) of guide cube or fixture (604), guide cube or fixture (704) is configured to slidably insert into multiple locating features (302), as seen in FIG. 14.

C. Method of Targeting a Single Orientation Guide Cube with the Open Recessed Grid Plate In the present example, grid plate (396) is a lateral fence that serves as a compression plate for holding a breast firmly in place. Grid plate (396), in conjunction with guide cube or fixture (604), is configured to refine the insertion point of the instrument (e.g., needle (90) of probe (91), obturator/cannula (92, 94), etc.) into a patient's breast for performing a biopsy procedure. As seen in FIG. 14, guide cube or fixture (604) is slidably inserted into grid plate (396) by directing guide holes (606, 608, 610) into any open recess (330) at any selective position along any horizontal bar (334) as an operator desires. In this instance, an operator is provided unrestricted access to a substantial area of the breast tissue due to the increased access and visibility provided by open recesses (330). With no vertical bars and fewer horizontal bars (334) included in grid plate (396), grid plate (396) provides greater visibility of the breast tissue through open recesses (330) such that an operator is able to easily see the area of interest when determining where along the tissue to insert the medical device. As such, an operator positions guide cube or fixture (604) at a corresponding location along grid plate (396) using X, Y, and Z dimensions that correspond to the coordinates of an identified lesion.

Guide holes (606, 610) are securely received by a top and bottom locating feature (320) such that guide cube or fixture (604) is laterally secured. Simultaneous with the insertion of guide cube or fixture (604) into grid plate (396), guide holes (606, 608, 610) securely fits against open recesses (330) through the frictional engagement created therebetween. In this instance, the combination of obturator (92) slid into cannula (94) is guided through guide cube or fixture (604) to the biopsy site within the breast tissue. Obturator (92) is then withdrawn from cannula (94), then needle (90) of probe (91) is inserted into cannula (94). Biopsy device (14) is then operated to acquire one or more tissue samples from the breast via needle (90).

In other versions as described above and shown in FIG. 19, with open recesses (330) not including locating features (302) along horizontal bars (334), guide holes (606, 608, 610) are inserted into open recesses (330) without guide cube or fixture (604) being securely fastened to grid plate (396) in either the vertical or horizontal direction. As such, guide cube or fixture (604) is freely translatable within open recesses (330) thereby allowing guide holes (606, 608, 610) to easily be positioned at a desired location along horizontal bar (334). In the present example, with guide holes (606, 608, 610) selectively maneuvered to a desired location within grid plate (396), guide cube or fixture (604) is maintained in position through the pressed fit against horizontal bars (334) thereby securely engaging guide cube or fixture (604) to grid plate (396) despite the absence of locating features (302).

D. Open Recessed Grid Plate with Recessed Locating Features

Figure 20:
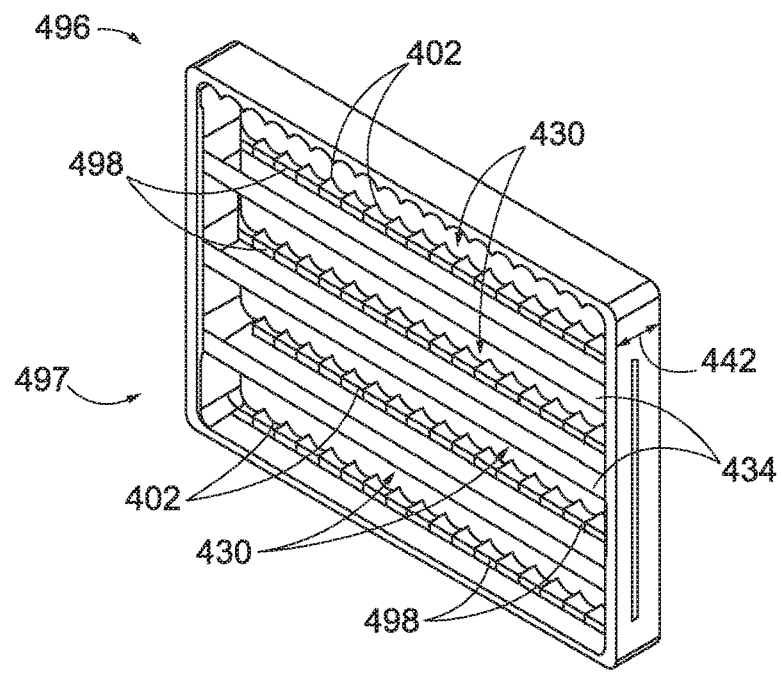
FIG. 20 depicts a perspective view of another exemplary alternative grid plate, including a series of horizontal bars and a plurality of recessed locating features.

FIG. 20 shows an exemplary alternative grid plate (496) for use in association with laterally adjustable outer three-sided plate bracket (98) as similarly described above. Except as otherwise provided below, grid plate (496) is configured and operable like grid plate (96, 396) described above. Grid plate (496) comprises horizontal bars (434) extending laterally across grid plate (496) thereby forming open recesses (430). Unlike grid plate (96), grid late (496) does not include a plurality of vertical bars (132) forming distinct square recesses at the intersections with horizontal bars (434). However, similar to grid plate (396), grid plate (496) may include one or more vertical bars while preserving the increased access and visibility created by the overall reduction of bars extending through open recesses (430).

Grid plate (496) further includes a plurality of locating features (402) extending along horizontal bars (434) and into open recesses (430). Locating features (302) are configured to correspond to a shape and size of guide cube or fixture (604, 704) such that locating features are operable to receive and securely hold guide cubes or fixtures (604, 704) therein. Locating features (402) are configured to be recessed from a proximal face (497) of grid plate (496), the proximal face (497) being opposite from a patient's tissue and proximate to an operator, such that locating features (402) are positioned along a middle portion of a thickness (442) of open recesses (430). With locating features (402) recessed from proximal face (497), a level surface (498) is formed along the middle portion of thickness (442) within open recesses (430).

Lateral surface (498) extends along the longitudinal length of horizontal bars (434) and is configured to receive and hold distal end (607, 707) of guide cube or fixture (604, 704). In this instance, with guide cube (604, 704) received in open recesses (430), and distal end (607, 707) resting along lateral surface (498), guide cube or fixture (604, 704) is operable to slidably translate along lateral surface (498) within open recesses (430). As such, grid plate (496) is configured to permit lateral maneuvering of guide cube or fixture (604, 704) within open recesses (430) by slidably translating guide holes (606, 608, 610, 706, 708, 710) along lateral surface (498) to a desirable location along horizontal bar (434).

Similar to locating features (302) of grid plate (396), locating features (402) are formed to have a concave profile configured to correspond to a convex shape of guide cube or fixture (604, 704) such that open recesses (430) are operable to fittingly receive guide cubes or fixtures (604, 704) between locating features (402). In this instance, locating features (402) provide a matching fit with guide holes (606, 608, 610, 706, 708, 710) which increases the surface area of guide cube or fixture (604, 704) that is contacted by grid plate (496). Locating features (402) are integral with grid plate (496) such that locating features (402) are formed of a hard, rigid plastic material. Although not shown, it should be understood that locating features (402) may be separate components attached to grid plate (496). Open recesses (430) are configured to provide greater space for grid plate (496) to receive certain targeting cubes that accommodate larger needle sizes that are not able to be received within other grid plates having smaller recesses, such as grid plate (96).

In the present example, guide cube or fixture (604, 704) is slidably inserted into grid plate (496) by directing guide holes (606, 608, 610, 706, 708, 710) into any open recess (430) at any selective position along any horizontal bar (434) as an operator desires. Guide cube (604, 704) is slidably translated within open recess (430) until guide cube (604, 704) is selectively positioned at a location along horizontal bar (434) that is ideal for performing the biopsy procedure. As guide cube or fixture (604, 704) is translated, distal end (607, 707) slidably contacts lateral surface (498) of open recess (430). With guide cube or fixture (604, 704) positioned at a desired location in relation to grid plate (496), a downward force is applied to proximal end (609, 709) to thereby direct distal end (607, 707) of guide cube or fixture (604, 704) beyond lip (439) and against narrowed opening (438). In this instance, guide holes (606, 608, 610, 706, 708, 710) are securely engaged to narrowed-opening (438) such that guide cube or fixture (604, 704) is in frictional contact with open recess (430), thereby removably holding guide cube or fixture (604, 704) to grid plate (496).

In other versions, grid plate (496) may include locating features (402) configured to be offset from a distal face (499) of grid plate (496), rather than recessed from proximal face (497) as described above. In this instance, distal face (499) is configured to be positioned adjacent to a patient's tissue and opposite of an operator. In the present example, locating features (402) extend between proximal face (497) and a middle portion of thickness (442) of open recesses (430). With locating features (402) offset from distal face (499) to a middle portion of thickness (442), lateral surface (498) is formed along the middle portion of thickness (442) within open recesses (430). As similarly discussed above, lateral surface (498) extends along the longitudinal length of horizontal bars (434) and is configured to receive and hold distal end (607, 707) of guide cube or fixture (604, 704). In this instance, with locating features (402) offset from distal face (499), grid plate (496) minimizes the likelihood of locating features (402) encountering or making contact with a patient's tissue.

In this instance, with guide cube (604, 704) received in open recesses (430), and distal end (607, 707) resting along lateral surface (498), guide cube or fixture (604, 704) is prevented from axially translating through open recesses (430). Furthermore, with grid holes (606, 608, 610, 706, 708, 710) slidably received between locating features (402), grid plate (496) is configured to prevent lateral translation of guide cube or fixture (604, 704) within open recesses (430).

E. Single Orientation Guide Cube with Edge Lip

Figure 21:
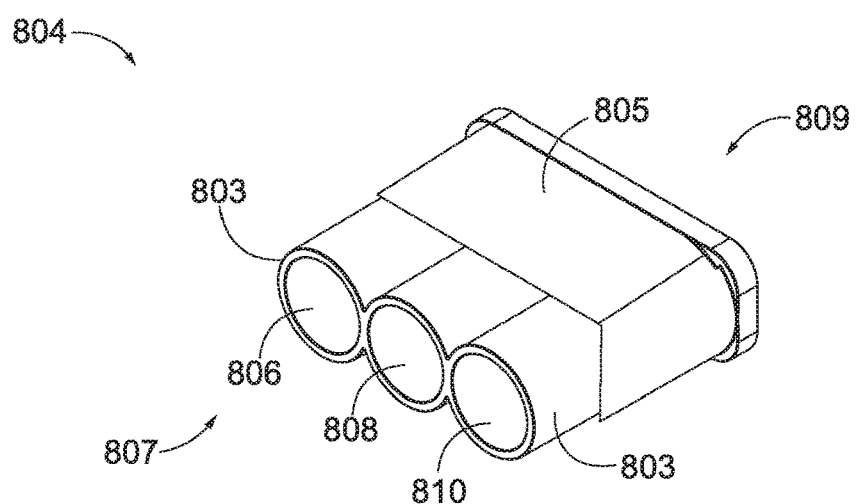
FIG. 21 depicts a perspective view of another exemplary alternative guide cube, including a single orientation of three guide holes and an edge lip extending therefrom.
Figure 22:
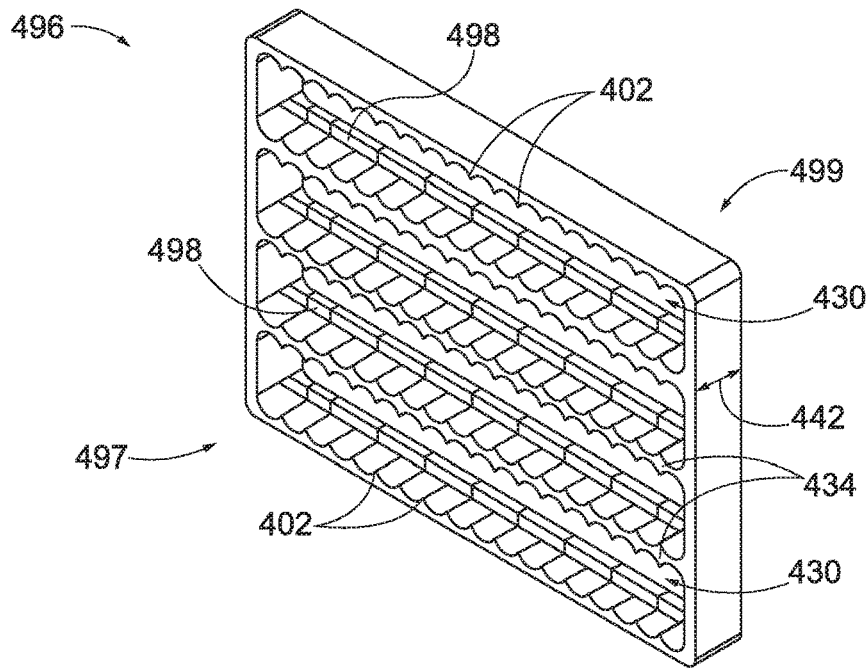
FIG. 22 depicts a perspective view of an exemplary variation of the grid plate of FIG. 20, including a flat distal face for compression against a tissue.
Figure 23:
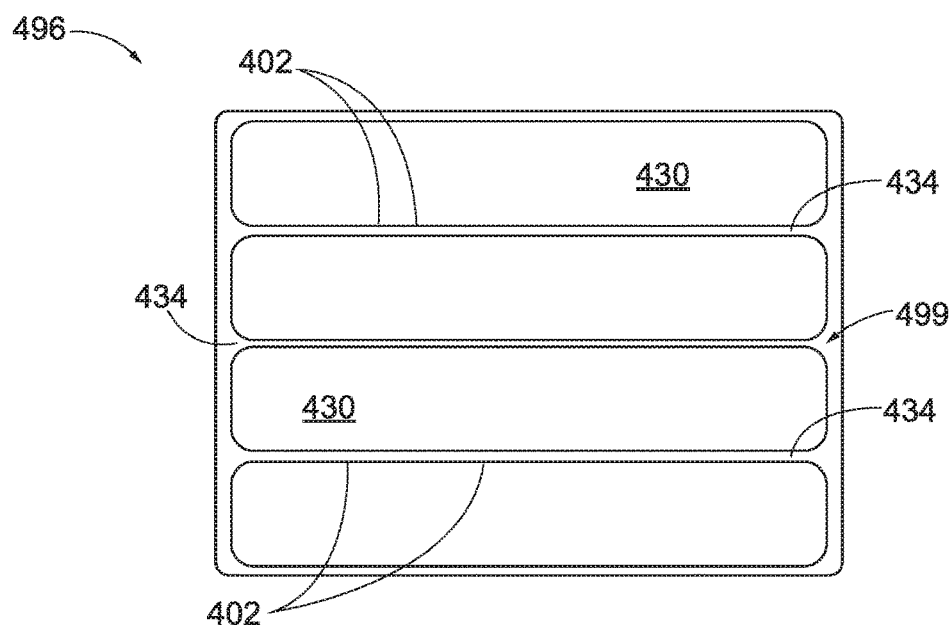
FIG. 23 depicts a rear elevational view of the grid plate of FIG. 22.

FIG. 21 shows an exemplary alternative guide cube or fixture (804). Except as otherwise provided below, guide cube or fixture (804) is configured and operable just like guide cube (607) described above. Guide cube or fixture (804) comprises guide holes (806, 808, 810) having a circular profile and positioned atop one another in a longitudinal arrangement. Although guide cube or fixture (804) is shown in a three-hole orientation, it should be understood that guide cube or fixture (804) may include more or less guide holes (806, 808, 810). As merely an illustrative example, guide cube or fixture (804) may include a nine-hole orientation similar to guide cube or fixture (704).

Guide cube or fixture (804) is sized and shaped for insertion into a proximal face of open recesses (430) of grid plate (496), opposite a distal face adjacent to the breast tissue. In the present example, guide cube or fixture (804) has a convex shape configured to correspond to the concave profile of locating features (402) of grid plate (496), such that guide cube or fixture (804) is configured to fit within locating features (402) and thereby be securely held by open recesses (430). Although not shown, it should be understood that guide cube or fixture (804) can have various shapes corresponding to the profile of locating features (402) of open recesses (430) as will be apparent to those of ordinary skill in the art.

Guide cube or fixture (804) includes an edge lip (803) extending laterally from guide holes (806, 808, 810) along a distal end (807) of guide cube or fixture (804). Edge lip (803) is configured to extend laterally from guide holes (806, 808, 810) at a minimal length to provide guide cube or fixture (804) additional support to slidably translate along lateral surface (498) of grid plate (496). However, the minimal extension of edge lip (803) from guide holes (806, 808, 810) is configured to still permit distal end (807) to enter beyond lip (440) of open recess (430) and into narrowed opening (438) of grid plate (496) when a downward force is applied to guide cube or fixture (804). In other words, edge lip (803) creates stability for guide cube or fixture (804) by providing a greater surface area along distal end (807) that contacts lateral surface (498) of grid plate (496).

Due to locating features (402) of the present example of grid plate (496) being recessed from the proximal face of grid plate (496), a space is formed between a guide cube or fixture slidably inserted into open recesses (430). In the present example, guide cube or fixture (804) further includes a housing or jobby (805) proximate to a proximal end (809). Jobby (805) extends along a proximal portion of guide cube or fixture (804) and encases a proximal portion of guide holes (806, 808, 810) therein. Jobby (805) is shaped and sized to create a physical grounding between guide cube or fixture (804) and the inner walls of horizontal bar (434) when guide cube or fixture (804) is slidably inserted into open recesses (430). In other words, jobby (805) has a thickness that is configured to correspond and fill the void between guide cube or fixture (804) and a proximal portion of horizontal bar (434) extending between a proximal face of grid plate (496) and lateral surface (498). Jobby (805) is operable to encounter locating features (402) when guide cube or fixture (804) is further inserted into open recesses (430) such that jobby (805) is configured to prevent guide cube or fixture (804) from slidably translating through open recesses (430) and out from a distal face of grid plate (496).

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical device localization assembly, comprising: (a) an exterior frame, wherein the exterior frame includes a distal face and a proximal face, wherein the distal face is configured to compress against tissue; (b) at least one lateral bar, wherein the at least one lateral bar extends within the exterior frame, wherein at least one open recess is formed between the at least one lateral bar and the exterior frame; (c) a plurality of locating members, wherein the plurality of locating members are positioned along an inner side of the exterior frame and the at least one lateral bar, wherein the plurality of locating members extend into the at least one open recess; and (d) a targeting guide, wherein the at least one open recess is configured to removably receive the targeting guide at the proximal face, wherein the plurality of locating members are sized and shaped to removably hold the guide cube such that the plurality of locating members are configured to correspond to the shape of the targeting guide.

Example 2

A medical device localization assembly of Example 1, wherein the plurality of locating members extend between the distal face and the proximal face.

Example 3

A medical device localization assembly of Example 2, wherein the plurality of locating members are integrally formed with the exterior frame.

Example 4

A medical device localization assembly of Example 2, wherein the at least one lateral bar is integrally formed with the exterior frame.

Example 5

A medical device localization assembly of Example 1, wherein the targeting guide is configured to removably fit within a pair of the plurality of locating members.

Example 6

A medical device localization mechanism of Example 1 through Example 3, wherein the exterior frame is formed of a rigid plastic material.

Example 7

A medical device localization assembly of Example 1, wherein the plurality of locating members have a rippled or waved profile extending into the at least one open recess.

Example 8

A medical device localization assembly of Example 1, wherein the plurality of locating members extend between the distal face and an intermediate portion of the exterior frame.

Example 9

A medical device localization assembly of Example 1 through Example 8, wherein the exterior frame includes a lateral surface at the intermediate portion, wherein the lateral surface extends along the inner side of the exterior frame and the at least one lateral bar.

Example 10

A medical device localization assembly of Example 8 through Example 9, wherein the lateral surface is configured to engage a front end of the targeting guide when slidably inserted into the at least open recess.

Example 11

A medical device localization assembly of Example 8 through Example 10, wherein the front end of the targeting guide is configured to slidably translate within the at least one open recess along the lateral surface.

Example 12

A medical device localization assembly of Example 8 through Example 11, wherein the distal face of includes a narrowed opening and/or lip configured to frictionally engage the front end such that the exterior frame is operable to securely retain the targeting guide.

Example 13

A medical device localization assembly of Example 8 through Example 11, wherein the targeting guide includes an edge lip along the front end, wherein the edge lip is configured to slidably translate along the lateral surface wherein the targeting guide further includes a housing configured to engage the lateral surface and prevent the targeting guide from sliding through the at least one open recess.

Example 14

A medical device localization assembly of Example 1, wherein the targeting guide includes at least one opening configured to receive a medical device therein.

Example 15

A medical device localization assembly of Example 1, further comprising at least one vertical bar extending within the exterior frame and intersecting the at least one lateral bar.

Example 16

A localization mechanism, comprising: (a) a grid fixture configured to guide a medical device; (b) a grid wall extending laterally through the grid fixture to form at least two receiving passages within the grid fixture, wherein the at least two receiving passages are configured to removably receive the medical device; and (c) a plurality of locating members, wherein the plurality of locating members extend inwardly from the grid wall into the at least two receiving passages, wherein each of the plurality of locating members extends toward an opposing locating member of the plurality of locating members, wherein the plurality of locating members are configured to engage the medical device within the at least two receiving passages.

Example 17

The localization mechanism of Example 16, further comprising a guide fixture configured to support and orient the medical device.

Example 18

The localization mechanism of Example 17, wherein the plurality of locating members are sized and shaped to removably retain the guide fixture within the at least two receiving passages.

Example 19

The localization mechanism of Example 17, wherein the grid fixture is operable to receive at least one of the guide fixture within the at least two receiving passages, wherein the grid fixture is configured to be received by a breast coil for tissue compression.

Example 20

A method of positioning a biopsy device at a desired tissue location, the method comprising: (a) compressing the localization grid against the tissue location; (b) inserting the guide fixture to a first position into one of the one or more open recesses; (c) sliding the guide fixture horizontally within the one or more open recesses to a desired biopsy site; (d) pushing the guide fixture to a second position further into the one or more open recesses to securely engage the guide fixture into the frame; and (e) inserting a medical device into the guide fixture to access the desired biopsy site.

VII. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A medical device localization assembly, comprising:
   (a) an exterior frame, wherein the exterior frame includes a distal face and a proximal face, wherein the distal face is configured to compress against tissue;
   (b) at least one lateral bar, wherein the at least one lateral bar extends within the exterior frame, wherein an open recess is formed between the at least one lateral bar and the exterior frame;
   (c) a plurality of locating members, wherein the plurality of locating members are positioned along an inner side of the exterior frame and the at least one lateral bar, wherein the plurality of locating members extend into the open recess; and
   (d) a targeting guide, wherein the open recess is configured to removably receive the targeting guide at the proximal face, wherein the targeting guide is configured to move laterally relative to the exterior frame for positioning at a targeting position, wherein the plurality of locating members are sized and shaped to selectively secure the targeting guide once the targeting guide is moved to the targeting position, wherein the plurality of locating members are configured to receive the targeting guide in a plurality of lateral positions within the open recess while the targeting guide remains engaged with the at least one lateral bar.

2. The medical device localization assembly of claim 1, wherein each locating member of the plurality of locating members is configured to correspond to the shape of the targeting guide.

3. The medical device localization assembly of claim 1, wherein the plurality of locating members extend between the distal face and the proximal face.

4. The medical device localization assembly of claim 1, wherein the at least one lateral bar is integrally formed with the exterior frame.

5. The medical device localization assembly of claim 1, wherein the targeting guide is configured to removably fit within a pair of the plurality of locating members.

6. The medical device localization mechanism of claim 3, wherein the exterior frame is formed of a rigid plastic material.

7. The medical device localization assembly of claim 1, wherein the plurality of locating members have a rippled or waved profile extending into the open recess.

8. The medical device localization assembly of claim 1, wherein the plurality of locating members extend between the distal face and an intermediate portion of the exterior frame.

9. The medical device localization assembly of claim 8, wherein the exterior frame includes a lateral surface at the intermediate portion, wherein the lateral surface extends along the inner side of the exterior frame and the at least one lateral bar.

10. The medical device localization assembly of claim 9, wherein the lateral surface is configured to engage a front end of the targeting guide when slidably inserted into open recess.

11. The medical device localization assembly of claim 10, wherein the front end of the targeting guide is configured to slidably translate within the open recess along the lateral surface.

12. The medical device localization assembly of claim 11, wherein the targeting guide includes an edge lip along the front end, wherein the edge lip is configured to slidably translate along the lateral surface.

13. The medical device localization assembly of claim 11, wherein the targeting guide includes a housing configured to engage the lateral surface and prevent the targeting guide from sliding through the open recess.

14. The medical device localization assembly of claim 1, wherein the targeting guide includes at least one opening configured to receive a medical device therein.

15. The medical device localization assembly of claim 1, further comprising at least one vertical bar extending within the exterior frame and intersecting the at least one lateral bar.

16. A localization mechanism, comprising:
(a) a grid fixture configured to guide a medical device;
(b) a grid wall extending laterally through the grid fixture to form at least two receiving passages within the grid fixture, wherein the at least two receiving passages are configured to removably receive the medical device; and
(c) a plurality of locating members, wherein the plurality of locating members extend inwardly from the grid wall into the at least two receiving passages, wherein each of the plurality of locating members extends toward an opposing locating member of the plurality of locating members, wherein the plurality of locating members are configured to engage the medical device within a selected receiving passage of the at least two receiving passages in a plurality of lateral positions while the medical device remains within the grid fixture.

17. The localization mechanism of claim 16, further comprising a guide fixture configured to support and orient the medical device.

18. The localization mechanism of claim 17, wherein the plurality of locating members are sized and shaped to removably retain the guide fixture within the at least two receiving passages.

19. The localization mechanism of claim 17, wherein the grid fixture is operable to receive at least one of the guide fixture within the at least two receiving passages, wherein the grid fixture is configured to be received by a breast coil for tissue compression.

\* \* \* \* \*